United States Patent [19]

Abdulla et al.

[11] 3,967,952
[45] July 6, 1976

[54] 3,5-DIPHENYL-4(1H)-PYRIDAZINONES(THIONES)

[75] Inventors: Riaz F. Abdulla, Greenfield; Quentin F. Soper, Indianapolis, both of Ind.

[73] Assignee: Eli Lilly and Company, Indianapolis, Ind.

[22] Filed: July 3, 1975

[21] Appl. No.: 593,096

[52] U.S. Cl. .............................. 71/92; 260/240 D; 260/250 A; 260/570.5 C
[51] Int. Cl.² .............. C07D 237/18; C07D 237/14; A01N 9/22; A01N 9/12
[58] Field of Search ...................... 260/250 A; 71/92

[56] References Cited
OTHER PUBLICATIONS

Breslow et al., J. Amer. Chem. Soc. 87, 1321–1325, (1965).

Izzo et al., Chem. and Ind., pp. 839–840, 1964.

*Primary Examiner*—Alton D. Rollins
*Assistant Examiner*—Mark L. Berch
*Attorney, Agent, or Firm*—Joseph A. Jones; Everet F. Smith

[57] ABSTRACT

A series of 3,5-diphenyl-4(1H)-pyridazinones and thiones are useful for reducing the vigor of unwanted herbaceous plants. The compounds are effective when applied either preemergence or postemergence to the unwanted plants. The compounds bear 1-alkyl substituents, and the phenyl rings may be substituted as well.

12 Claims, No Drawings

3,5-DIPHENYL-4(1H)-PYRIDAZINONES(THIONES)

BACKGROUND OF THE INVENTION

This invention belongs to the field of agricultural chemistry, and provides to the art a new method of reducing the vigor of unwanted herbaceous plants. The growth of plants out of place has well-known deleterious effects on crops which are infested with such plants. Unwanted plants growing in cropland, as well as in fallow land, consume soil nutrients and water. Thus, such plants constitute a serious drain on the resources of the soil, and also shade crop plants from the sun.

The compounds of this invention are new to organic chemistry, although some pyridazinones have been disclosed before. For example, Breslow et al., "Diphenylcyclopropenone", *J. Am. Chem. Soc.* 87, 1321–25 (1965), and Izzo et al., "Reaction of Diazomethane with Cyclopropenones", *Chem. J Ind.* 839–40 (1964), disclosed processes for making 3,5-diphenyl-4(1H)-pyridazinone. This compound, without a 1-alkyl substituent, is not a useful herbicide.

Some pyridazinones have found use in agricultural chemistry. For example, 4-chloro-5-methylamino-2-($\alpha,\alpha,\alpha$-trifluoro-m-tolyl)-3(2H)-pyridazinone is a marketed herbicide. U.S. Pat. No. 3,644,355. East German Pat. No. 105,446 disclosed 1-phenyl-6-pyridazinones having halogen or amino substituents at the 4- and 5-positions which were said to be selective herbicides.

SUMMARY OF THE INVENTION

This invention provides to the agricultural chemical art new compounds of the formula:

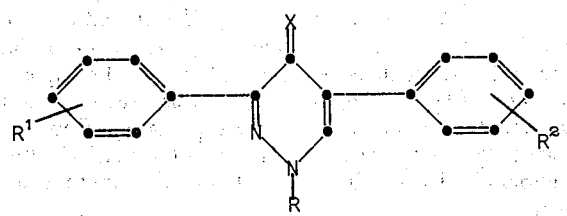

wherein
X represents oxygen or sulfur;
R represents $C_1-C_3$ alkyl;
$R^1$ and $R^2$ independently represent hydrogen, trifluoromethyl, fluoro, chloro, bromo or methyl.

DESCRIPTION OF THE PREFERRED EMBODIMENT

The following compounds of this invention are presented to assure that those of skill in the art understand the invention. The compounds below do not, of course, bound the invention, but are merely exemplary of it.

1-methyl-5-phenyl-3-($\alpha,\alpha,\alpha$-trifluoro-o-tolyl)-4(1H)-pyridazinone
1-ethyl-5-phenyl-3-(3-fluorophenyl)-4(1H)-pyridazinone
1-methyl-3-phenyl-5-($\alpha,\alpha,\alpha$-trifluoro-p-tolyl)-4(1H)-pyridazinethione
5-(2-chlorophenyl)-3-phenyl-1-propyl-4(1H)-pyridazinethione
1-ethyl-5-(3-fluorophenyl)-3-phenyl-4(1H)-pyridazinone
1-isopropyl-5-phenyl-3-($\alpha,\alpha,\alpha$-trifluoro-m-tolyl)-4(1H)-pyridazinethione
3-(2-chlorophenyl)-5-phenyl-1-propyl-4(1H)-pyridazinone
1-ethyl-3-(2-fluorophenyl)-5-phenyl-4(1H)-pyridazinone
3-(4-chlorophenyl)-1-methyl-5-($\alpha,\alpha,\alpha$-trifluoro-m-tolyl)-4(1H)-pyridazinone
5-(3-chlorophenyl)-1-methyl-3-phenyl-4(1H)-pyridazinone
3-(3-chlorophenyl)-5-(4-fluorophenyl)-1-methyl-4(1H)-pyridazinethione
3-(m-tolyl)-5-phenyl-1-propyl-4(1H)-pyridazinethione
3-(3-bromophenyl)-1-ethyl-5-phenyl-4(1H)-pyridazinone
3-(4-fluorophenyl)-5-phenyl-1-propyl-4(1H)-pyridazinethione
5-(4-bromophenyl)-1-isopropyl-3-phenyl-4(1H)-pyridazinethione
5-(4-chlorophenyl)-1-methyl-3-phenyl-4(1H)-pyridazinethione
1-ethyl-3-(m-tolyl)-5-($\alpha,\alpha,\alpha$-trifluoro-m-tolyl)-4(1H)-pyridazinone
1-isopropyl-5-phenyl-3-(p-tolyl)-4(1H)-pyridazinone
5-(3-fluorophenyl)-1-methyl-3-($\alpha,\alpha,\alpha$-trifluoro-p-tolyl)-4(1H)-pyridazinethione
3-(2-bromophenyl)-5-phenyl-1-propyl-4(1H)-pyridazinone
5-(3-bromophenyl)-1-ethyl-3-phenyl-4(1H)-pyridazinethione
1-ethyl-5-(m-tolyl)-3-($\alpha,\alpha,\alpha$-trifluoro-o-tolyl)-4(1H)-pyridazinone
5-(3-bromophenyl)-3-(2-chlorophenyl)-1-methyl-4(1H)-pyridazinethione
1-methyl-3-phenyl-5-(o-tolyl)-4(1H)-pyridazinethione
5-(2-chlorophenyl)-1-methyl-3-($\alpha,\alpha,\alpha$-trifluoro-m-tolyl)-4(1H)-pyridazinone
5-(4-chlorophenyl)-1-ethyl-3-(3-fluorophenyl)-4(1H)-pyridazinone
3-phenyl-1-propyl-5-(m-tolyl)-4(1H)-pyridazinethione
5-(3-bromophenyl)-1-ethyl-3-(o-tolyl)-4(1H)-pyridazinone
5-(4-bromophenyl)-1-isopropyl-3-($\alpha,\alpha,\alpha$-trifluo-m-tolyl)-4(1H)-pyridazinone
5-(4-fluorophenyl)-1-methyl-3-(o-tolyl)-4(1H)-pyridazinone
3-(3-bromophenyl)-5-(4-chlorophenyl)-1-methyl-4(1H)-pyridazinethione
3-(4-chlorophenyl)-1-ethyl-5-(m-tolyl)-4(1H)-pyridazinethione The preferred compounds of this invention are 1-methyl-5-phenyl-3-($\alpha,\alpha,\alpha$-trifluoro-m-tolyl)-4(1H)-pyridazinone, 1-methyl-3,5-diphenyl-4(1H)-pyridazinone, 3,5-diphenyl-1-propyl-4(1H)-pyridazinone, 1-ethyl-3,5-diphenyl-4(1H)-pyridazinone, and 3-(3-bromophenyl)-1-methyl-5-phenyl-4(1H)-pyridazinone.

Both Izzo et al., and Breslow et al., cited above, prepared 1-unsubstituted compounds similar to those of this invention by the reaction of diazomethane with diphenylcyclopropenone. The compounds of this invention, however, are best prepared by means of the following novel synthesis scheme.

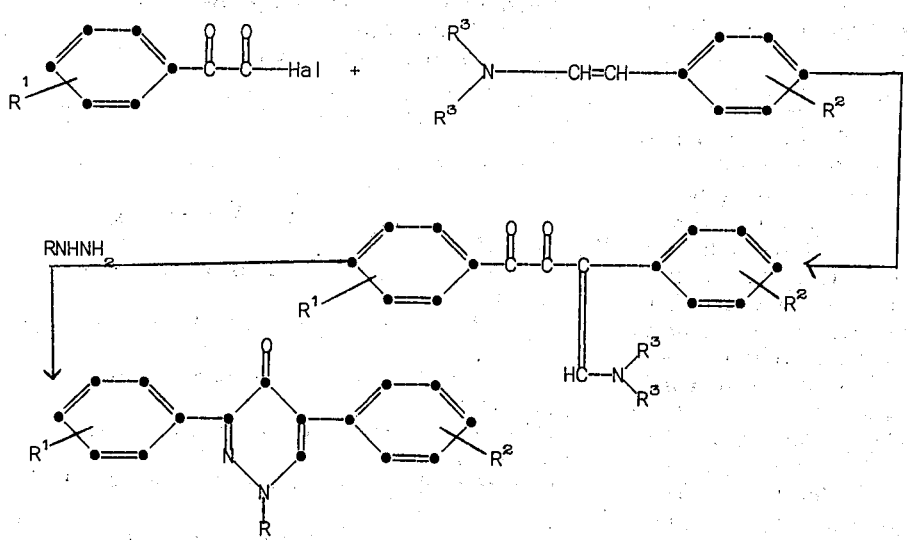

In the first step, a phenylglyoxyloyl halide is reacted with a styrylamine. In the second step, the enaminoketone formed in the first step is reacted with an alkylhydrazine to close the ring and form the pyridazinone. If desired, the second step may be performed with hydrazine instead of an alkylhydrazine, forming the 1-unsubstituted pyridazinone, which is then akylated as described below. The two steps may be performed without isolation of the intermediate.

The term Hal represents fluoro, chloro, bromo or iodo.

In the above formula the $R^3$ groups independently represent $C_1$–$C_3$ alkyl, or the $R^3$ groups combine with the nitrogen atom to which they are attached to form heterocyclic rings such as azetidine, pyrrolidine, piperidine or morpholine. The $R^3$ groups do not enter into the reaction, but carry through the reaction scheme unchanged. The $R^1$ and $R^2$ substituents are not affected by the reaction, and so the $R^1$ and $R^2$ substituents of the desired product are readily provided by the corresponding substituents of the starting compounds.

The starting compounds are obtainable by processes known in the art. The phenylglyoxyloyl halides are made from correspondingly substituted acetophenones. First, the ketone is oxidized with an agent such as potassium permanganate in aqueous pyridine at a temperature in the range of 10°–15°C. to form the correspondingly substituted glyoxylic acids in economical yields. The halides are then made from the glyoxylic acids by reaction with a halogenating agent, such as thionyl chloride or bromide for example, in an inert solvent such as benzene or chloroform. The desired halide is easily recovered by stripping the solvent.

The styrylamines are readily made by the amination of an appropriately ring-substituted phenylacetaldehyde with a secondary amine bearing the substituents described as $R^3$ in the reaction scheme above.

The first step of the synthesis is carried out in the presence of a proton scavenger which may be a tertiary amine such as triethylamine or pyridine, or may be an anion exchange resin. The solvent for the first step reaction may be any aprotic solvent which is a liquid at the reaction temperature. The preferred reaction solvent is diethyl ether; aromatic solvents such as benzene and toluene, aliphatic solvents such as hexane, and halogenated solvents such as chloroform are also perfectly satisfactory. The reaction temperature is in the range of from about −10°C. to about 30°C. The preferred temperature range is from about 0°C. to about 10°C.

In the second step of the synthesis, the enaminoketone formed in the first step is reacted with a $C_1$–$C_3$ alkylhydrazine, or with hydrazine. In either case, the preferred reaction solvent is a mixture of diethyl ether and a lower alkanol. The reaction solvent is not critical, however, and may be any convenient solvent chosen from the alcohols such as methanol and isopropanol, the ethers such as diethyl ether and tetrahydrofuran, the halogenated solvents such as methylene chloride, the aromatics such as benzene and xylene, the aliphatics such as hexane and octane, the carboxamides such as dimethylformamide, and mixtures thereof. The preferred reaction temperature is about 20°–25°C., but temperatures from about 0° to about 40°C. are satisfactory.

Alkylation of a 1-unsubstituted pyridazinone is readily performed according to the common methods. Alkylation with an alkyl halide in the presence of sodium hydride in dimethylformamide is preferred, the the alkylation may also be handily performed with an alkyl iodide or a dialkyl sulfate in the presence of an alkali metal hydroxide.

When a pyridazinethione is the desired product, the keto oxygen is replaced with a thione atom by contact with $P_2S_5$ in pyridine, according to the known procedures.

The following preparative examples are shown to assure that organic chemists can easily obtain compounds of this invention.

The first example illustrates the preparation of the intermediate enamines.

EXAMPLE 1

1-diethylamino-2,4-diphenyl-1-buten-3,4-dione

Seven grams of N,N-diethylstyrylamine was dissolved in 100 ml. of diethyl ether and the solution was cooled to 0°C. Four grams of anhydrous triethylamine was added. A 7 g. portion of phenylglyoxyloyl chloride was dissolved in 50 ml. of diethyl ether and the solution was added dropwise, with stirring, to the first solution over about 75 minutes. As soon as the addition was complete, the reaction mixture was filtered, and the precipitated amine hydrochloride was washed with an additional 50 ml. of diethyl ether. The filtrate contained the intermediate enamine, 1-diethylamino-2,4-diphenyl-1-buten-3,4-dione, in dissolved form, and was used in the next step of the synthesis without purification.

EXAMPLE 2

3,5-diphenyl-4(1H)-pyridazinone

The product solution from Example 1 was cooled to 0°C. and mixed with 20 ml. of isopropyl alcohol and 2 ml. of hydrazine. The mixture was stirred for 10 minutes, and was then warmed to room temperature and stirred for 15 hours. The product was then collected by filtration. The yield was 6.0 g. of 3,5-diphenyl-4(1H)-pyridazinone, m.p. 328°–32°C., which was identified by infrared and nuclear magnetic resonance analysis.

The next example illustrates the alkylation of a 1-unsubstituted pyridazinone.

EXAMPLE 3

1-ethyl-3,5-diphenyl-4(1H)-pyridazinone

A 1 g. portion of the product of Example 2 was suspended in 40 ml. of dimethylformamide, the suspension was cooled under nitrogen to 0°–5°C., and an 0.3 g. portion of 50 percent NaH in oil was added. The reaction mixture was stirred for 30 minutes, and 3 ml. of ethyl iodide was added. The mixture was stirred at 0°–5°C. for 24 hours, and the mixture was then filtered to separate the precipitated product. The dried product was 1.0 g. of 1-ethyl-3,5-diphenyl-4(1H)-pyridazinone, m.p. 124°–25°C., which was identified by nuclear magnetic resonance analysis, infrared analysis, and mass spectrometry.

The following example illustrates the synthesis of a 1-alkyl pyridazinone directly using an alkyl hydrazine.

EXAMPLE 4

1-methyl-3,5-diphenyl-4(1H)-pyridazinone

A diethyl ether solution of the diphenyl enamine intermediate was produced by following exactly the procedure of Example 1. To the cool solution was added 2 ml. of methylhydrazine, and the mixture was stirred overnight. The solution was then washed with 2N HCl, with 2N KOH, and with water, and was then dried over anhydrous magnesium sulfate. It was then evaporated under vacuum to produce an oil which crystallized from isopropyl alcohol to produce 1.05 g. of 1-methyl-3,5-diphenyl-4(1H)-pyridazinone, m.p. 165°–67°C., which was identified by nuclear magnetic resonance analysis.

The next example illustrates the preparation of a pyridazinethione product.

EXAMPLE 5

1-methyl-3,5-diphenyl-4(1H)-pyridazinethione

A 1 g. portion of the product of Example 4 was dissolved in 10 ml. of pyridine and heated under reflux for 4 hours with 1 g. of $P_2S_5$. The solution was then poured into ice water and stirred for 30 minutes. The precipitate was recovered by filtration and crystallized from hexane-isopropyl alcohol. The yield was 1 g. of 1-methyl-3,5-diphenyl-4(1H)-pyridazinethione, m.p. 122°–23°C., which was identified by infrared, nuclear magnetic resonance and ultraviolet analyses, and by mass spectrometry.

The above synthetic procedures are used, with minor changes as necessary, to produce all of the compounds of this invention, such as the following additional examples.

EXAMPLE 6

3,5-diphenyl-1-propyl-4(1H)-pyridazinone, m.p. 90°–93°C.

EXAMPLE 7

3-(4-bromophenyl)-1-methyl-5-phenyl-4(1H)-pyridazinone, m.p. 159°–60°C.

EXAMPLE 8

1-methyl-5-phenyl-3-($\alpha,\alpha,\alpha$-trifluoro-m-tolyl)-4(1H)-pyridazinone, m.p. 110°–12°C.

The compounds described above have been tested in a number of herbicidal test systems to determine the range of their herbicidal efficacy. The results produced by the compounds in the representative tests reported below are exemplary of the activity of the compounds.

Compound application rates are expressed in kilograms of the compound per hectare of land (kg./ha.) throughout this specification and claims.

Blank spaces in the tables below indicate that the compound was not tested against the named species. In the tests below, plants were rated on a 1–5 scale, on which 1 indicates normal plants and 5 indicates dead plants or no emergence. The compounds are identified by their example numbers.

TEST 1

Broad Spectrum Greenhouse Test

Square plastic pots were filled with a sandy sterilized greenhouse soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test.

The table below reports results of testing typical compounds of the invention.

| Compound of Example No. | Preemergence | | | Postemergence | | |
|---|---|---|---|---|---|---|
| | Tomato | Large Crabgrass | Pigweed | Tomato | Large Crabgrass | Pigweed |
| 3 | 1 | 1 | 1 | 1 | 1 | 1 |
| 4 | 4 | 4 | 4 | 5 | 4 | 2 |
| 5 | 2 | 2 | 1 | 4 | 2 | 3 |
| 6 | 2 | 4 | 4 | 2 | 3 | 2 |
| 7 | 1 | 1 | 3 | 3 | 2 | 2 |

TEST 2

Seven-species Greenhouse Test

The test was conducted in general like the test above. The seeds were planted in flat metal trays, rather than in pots. The compounds were formulated according to the procedure above, except that about 6 g./100 ml. of the compound was dissolved in the surfactant-containing solvent, and about 1 part of the organic solution was diluted with 12 parts of water before application to the trays. The compounds were applied at the rate of 9.0 kg./ha., and the results of testing against the species named below are as follows.

| Compound of Example No. | Rate of Appln. kg./ha. | Preemergence | | | | | | | Postemergence | | | | | | |
|---|---|---|---|---|---|---|---|---|---|---|---|---|---|---|---|
| | | Corn | Large Crabgrass | Pigweed | Foxtail | Velvetleaf | Morning Glory | Zinnia | Corn | Large grass | Crabweed | Pigtail | Foxleaf | Morning Velvet-Glory | ing Zinnia |
| 3 | 9.0 | 1 | 3 | 3 | 2 | 2 | 1 | 1 | 1 | 1 | 1 | 1 | 1 | 2 | 1 |
| 4 | 9.0 | 1 | 3 | 3 | 2 | 1 | 1 | 1 | 1 | 1 | 1 | 1 | 1 | 1 | 1 |
| 5 | 9.0 | 1 | 1 | 1 | 1 | 1 | 1 | 1 | 1 | 1 | 1 | 1 | 1 | 1 | 1 |
| 6 | 9.0 | 1 | 2 | 3 | 2 | 1 | 1 | 1 | 1 | 1 | 1 | 1 | 1 | 1 | 1 |
| 7 | 9.0 | 1 | 1 | 2 | 2 | 1 | 1 | 1 | 1 | 1 | 1 | 1 | 1 | 1 | 1 |
| 8 | 9.0 | 3 | 5 | 4 | 4 | 3 | 2 | 1 | 3 | 2 | 2 | 3 | 3 | 3 | 2 |

TEST 3

Resistant Weed Tests

Typical compounds were evaluated in a test system which determined their ability to reduce the vigor of weeds which are resistant to many herbicides. The compounds were formulated and dispersed, and the dispersions were applied, as described in Test 1 above. The application rate was 9.0 kg./ha. in all of the tests reported here.

| Compound of Example No. | Preemergence | | | Postemergence | |
|---|---|---|---|---|---|
| | Yellow Nutsedge | Garden Huckleberry | Sicklepod | Ragweed | Yellow Nutsedge |
| 3 | 1 | 2 | 1 | 1 | 1 |
| 4 | 1 | 1 | 1 | 1 | 1 |
| 5 | 1 | 1 | 1 | 1 | 1 |
| 6 | 1 | 3 | 1 | 1 | 1 |
| 7 | 1 | 1 | 1 | 1 | 1 |
| 8 | 2 | 3 | 3 | 5 | 1 |

The broad-spectrum activity of the compounds of this invention is clearly illustrated by the above examples. The test results point up the efficacy of the compounds against annual grasses, the relatively easily-controlled broadleaves such as pigweed, and the more resistant broadleaves such as nightshades. Plant scientists will recognize that the exemplified activity of the compounds shows that the compounds are broadly effective against herbaceous weeds.

As the above test results demonstrate, the compounds are used to reduce the vigor of unwanted herbaceous plants by contacting the plants with an herbicidally-effective amount of one of the compounds described above. In some instances, as is clear from the test results, the whole population of the contacted plant is killed. In other instances, part of the plants are killed and part of them are injured, and in still other instances, none of the plants are killed but are merely injured by application of the compound. It will be understood that reducing the vigor of the unwanted plant population by injuring part of the plants is beneficial, even though part of the plant population survives application of the compound. The plants, the vigor of which has been reduced, are unusually susceptible to the stresses, such as disease, drought, lack of nutrients and so forth, which normally afflict plants.

Thus, the treated plants, even though they survive application of the compound, are likely to expire due to stress of the environment. Further, if the treated plants are growing in cropland, the crop, growing normally, tends to shade out the treated plants of reduced vigor. The crop, therefore, has a great advantage over the treated unwanted plants in the competition for nutrients and sunlight. Still further, when the treated plants are growing in fallow land, or industrial property which is desired to be bare, the reduction in their vigor necessarily tends to minimize the treated plants' consumption of water and nutrients, and also minimizes the fire hazard and nuisance which the plants present.

The compounds are herbicidally effective when applied both preemergence and postemergence. Thus, they can be applied to the soil to kill and injure weeds by soil contact when the weed seeds are germinating and emerging, and can also be used to kill and injure growing weeds by direct contact with the exposed portions of the weeds Preemergence application of the compounds, wherein the germinating and emerging plants are contacted with the compound through soil application, is preferred.

The best application rate of a given compound of the invention for the control of a given weed varies, of course, depending upon the climate, soil type, water and organic matter contents of the soil and other factors known to those skilled in plant science. It will be found, however, that the optimum application rate is usually in the range from about 2.0 to about 20 kg./ha.

It is not implied, of course, that all compounds of this invention are effective against all plants at all rates. Some compounds are more effective against some types of plants, other compounds are more effective against other types. All of the compounds, however, are effective against at least some herbaceous plants. It is within the ordinary skill of a plant scientist to ascertain the plants which are most advantageously controlled with the various compounds.

The compounds are applied to the soil or to emerged weeds in the manners usual in agriculture. It is best to apply the compounds in the form of the herbicidal compositions which are important embodiments of the present invention. They may be applied to the soil in the form of either water-dispersed or granular compositions, the preparation of which will be discussed below. Usually, water-dispersed compositions will be used for the application of the compounds to emerged weeds. The compositions are applied with any of the many types of sprayers and granular applicators which are in wide use for the distribution of agricultural chemicals over soil or standing vegetation. In general, the compositions are formulated in the manners usual in agricultural chemistry.

Very often, the compounds are formulated as concentrated compositions which are applied either to the soil or the foilage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier, and surfactants. The concentration of the compound is usually from about 10 percent to about 90 percent. The inert carrier is usually chosen from among the attapulgite clays, the montmorillonite clays, the kaolin clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable.

We claim:

1. A compound of the formula:

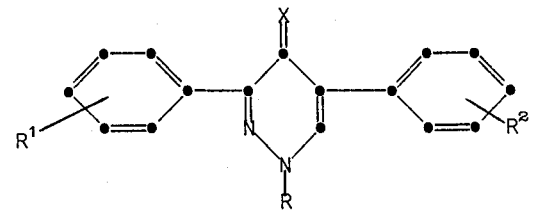

wherein
X represents oxygen or sulfur;
R represents $C_1-C_3$ alkyl;
$R^1$ and $R^2$ independently represent hydrogen, trifluoromethyl, fluoro, chloro, bromo or methyl.

2. The compound of claim 1 which is 1-methyl-5-phenyl-3-($\alpha,\alpha,\alpha$-trifluoro-m-tolyl)-4-(1H)-pyridazinone.

3. The compound of claim 1 which is 1-methyl-3,5-diphenyl-4(1H)-pyridazinone.

4. The compound of claim 1 which is 3,5-diphenyl-1-propyl-4(1H)-pyridazinone.

5. The compound of claim 1 which is 1-ethyl-3,5-diphenyl-4(1H)-pyridazinone.

6. The compound of claim 1 which is 3-(3-bromophenyl)-1-methyl-5-phenyl-4(1H)-pyridazinone.

7. An herbicidal composition which compromises a herbicidally active quantity of a compound of claim 1 and an inert carrier.

8. The composition of claim 7 wherein the compound is 1-methyl-5-phenyl-3-($\alpha,\alpha,\alpha$,-trifluoro-m-tolyl)-4(1H)-pyridazinone.

9. The composition of claim 7 wherein the compound is 1-methyl-3,5-diphenyl-4(1H)-pyridazinone.

10. The composition of claim 7 wherein the compound is 3,5-diphenyl-1-propyl-4(1H)-pyridazinone.

11. The composition of claim 7 wherein the compound is 1-ethyl-3,5-diphenyl-4(1H)-pyridazinone.

12. The composition of claim 7 wherein the compound is 3-(3-bromophenyl)-1-methyl-5-phenyl-4(1H)-pyridazinone.

* * * * *